(12) United States Patent
Salcedo et al.

(10) Patent No.: US 8,235,892 B2
(45) Date of Patent: Aug. 7, 2012

(54) LARYNGOSCOPE DENTAL PROTECTION DEVICE

(76) Inventors: Eduardo Salcedo, Bethesda, MD (US); Marta Mondino, McLean, VA (US)

( * ) Notice: Subject to any disclaimer, the term of this patent is extended or adjusted under 35 U.S.C. 154(b) by 364 days.

(21) Appl. No.: 11/696,992

(22) Filed: Apr. 5, 2007

(65) Prior Publication Data

US 2007/0235040 A1  Oct. 11, 2007

Related U.S. Application Data

(60) Provisional application No. 60/744,476, filed on Apr. 7, 2006.

(51) Int. Cl.
*A61B 1/267* (2006.01)
(52) U.S. Cl. ....................................................... 600/195
(58) Field of Classification Search .................. 600/185, 600/186, 194, 195; 211/59.2; 221/188, 186; 428/354
See application file for complete search history.

(56) References Cited

U.S. PATENT DOCUMENTS

| | | | | |
|---|---|---|---|---|
| 3,939,508 | A * | 2/1976 | Hall et al. .......................... | 5/727 |
| 4,583,527 | A * | 4/1986 | Musicant et al. ............. | 600/195 |
| 5,065,738 | A * | 11/1991 | Van Dam ....................... | 600/185 |
| 5,084,005 | A * | 1/1992 | Kachigian .......................... | 604/1 |
| 5,438,976 | A * | 8/1995 | Nash ............................ | 600/186 |
| 5,628,483 | A * | 5/1997 | Smith et al. .................... | 248/118 |
| 5,776,053 | A * | 7/1998 | Dragisic et al. ............... | 600/195 |
| 5,817,704 | A * | 10/1998 | Shiveley et al. .................. | 521/63 |
| 5,935,058 | A * | 8/1999 | Makita et al. ................. | 600/200 |
| 6,116,684 | A * | 9/2000 | Williams ....................... | 297/214 |
| 6,213,343 | B1 * | 4/2001 | Damikolas ....................... | 221/25 |
| 2003/0018239 | A1 * | 1/2003 | Cartledge et al. ............. | 600/195 |

OTHER PUBLICATIONS

Compression testing performed on product.

* cited by examiner

*Primary Examiner* — Kevin T Truong
*Assistant Examiner* — Christian Sevilla
(74) *Attorney, Agent, or Firm* — McNeely, Hare & War LLP; Kevin J. McNeely

(57) ABSTRACT

A dental protection device for a laryngoscope includes an elongated pad with a top surface and a bottom surface, an adhesive applied to the bottom surface and a pull-tab attached to the pad.

9 Claims, 5 Drawing Sheets

LARYNGOSCOPE DENTAL PROTECTION DEVICE

CROSS-REFERENCE TO RELATED APPLICATIONS

This utility patent application claims priority to U.S. Provisional Patent Application Ser. No. 60/744,476 filed on Apr. 7, 2006, which is incorporated by reference herein.

TECHNICAL FIELD

This invention is related to medical devices, and, more particularly, to a device that prevents mouth and dental trauma during a laryngoscopic procedure.

BACKGROUND

Endotracheal intubation is a procedure performed during the induction of general anesthesia. The patient is rendered unconscious with intravenous medications. With the patient asleep and paralyzed, the mouth is opened and a laryngoscope, which includes a handle with a light source connected to a straight or curved steel blade, is used to insert an endotracheal tube. The blade is inserted in the patient's mouth and the tongue is lifted and swept to the left side of the mouth. The blade is then further inserted to access the laryngeal structures and it is lifted in an upward motion to expose the vocal cords.

The light from the laryngoscope handle illuminates the vocal cords opening in order to see as the endotracheal tube is inserted into the trachea. This allows direct access to the lungs. At this point, a patient can be safely ventilated with oxygen and anesthetic gases and is kept asleep for a surgical procedure.

Laryngoscopy is not always a simple procedure. Patients have various anatomical differences that may complicate the insertion of an endotracheal tube. These complications range from devastating outcomes such as anoxia (lack of oxygen to the brain) to less life-threatening outcomes such as mouth and dental trauma. Dental trauma, in particular, is a common complication that occurs during the administration of general anesthesia.

Some patients have what is known as a "difficult airway". That is, they may have short mandibles (no chin), small mouths, large tongues, prominent upper incisors and/or fat "bull" necks (double chin). Treating a patient with a difficult airway is when dental trauma occurs most frequently since the upper teeth are positioned very close to the laryngoscope blade when used to intubate the trachea for the induction of general anesthesia. When the laryngoscope blade is inserted into the mouth, the flange of the blade can come in contact with the upper teeth. If the airway anatomy is such that the space for pushing the tongue and laryngeal structure away from the vocal cords opening is small, then the practitioner may attempt to force the structures aside by using the upper teeth as a fulcrum and torque the laryngoscope blade in the effort to expose the vocal cords. This pressure on the upper teeth commonly results in chipped teeth, dislodgment of caps and bridges or complete breaking of one or more teeth. Although not a life threatening occurrence, this outcome has become a common reason for lawsuits against anesthesia practitioners.

In order to prevent this type of dental trauma, there have been modifications to laryngoscope blades to minimize damage to the teeth. The modified blades include curved and angled blades that allow for improved visualization with less torquing of the laryngoscope. However, the steel flange may still come into contact with the teeth.

Tooth guards, such as for example, sports guards, may also be used, however, they may not fit well and have the potential to move during intubation causing distraction and reduced visualization. Other devices have been used to prevent direct dental contact with the steel blade, however, these devices can be complex, cumbersome or can consume too much time or be impractical to apply in a real clinical setting, particularly during an emergency when ventilation is needed immediately.

SUMMARY

The dental protection device is applied to a laryngoscope blade to prevent or minimize tooth and/or mouth trauma, particularly damage to the upper teeth.

In one general aspect, a dental protection device for a laryngoscope includes an elongated pad with a top surface and a bottom surface, an adhesive applied to the bottom surface and a pull-tab attached to the pad.

Embodiments may include one or more of the following features. For example, the pad may have a rectangular shape and it may be made of closed-cell foam. The pad may also be made of multiple layers that are bonded or laminated together. As an additional feature, the pad may be tapered with one end being thin and the other end being thick, with the pull-tab attached to the thick end. The laminated layers may have a compression strength of 6-8 PSI @ 25% and 17-20 PSI @ 50%.

In another general aspect, a dental protection system for endotracheal intubation during an anesthesia procedure includes more than one dental protection device, with each device including an elongated pad with a top surface and a bottom surface, an adhesive applied to the bottom surface and a pull-tab attached to the elongated pad. The system also includes a rectangular strip with a non-stick surface. A plurality of the dental protection devices are positioned on the non-stick surface.

Embodiments may include one or more of the above or following features. For example, the system may include a removable liner that covers the non-stick surface and the dental protection devices.

As another feature, the system may include a rectangular box and a dowel positioned inside the box and attached to the sides of the box so that it freely rotates. The rectangular strip is wrapped around the dowel to store the dental protection devices. There may be a channel located anywhere on the box to dispense the dental protection devices.

In still another general aspect, a method of using a dental protection device for endotracheal intubation during an anesthesia procedure includes separating a package liner from a back panel of the package to expose the dental protection device, grasping the pull-tab, pulling the pull-tab back to remove the dental protection device from the panel and positioning the dental protection device on a laryngoscope with the adhesive backing in contact with the blade of the laryngoscope.

Embodiments may include one or more of the above or following features. For example, the method may include applying a second dental protection device to the opposing side of the blade.

In a further general aspect, a method of manufacturing a tooth protection device includes laminating foam layers together as a foam panel, die-cutting the foam panel into elongated pads, applying an adhesive to a at least a portion of the bottom surface of the elongated pads and attaching a pull-tab to each bottom surface.

Embodiments may include one or more of the above or following features. For example, the method may include sealing the dental protection device in a plastic pouch. Alternatively, the method includes positioning more than one tooth protection device on a non-stick strip and wrapping the non-stick strip around a dowel that rotates inside a box.

DETAILED DESCRIPTION

Figure 1:
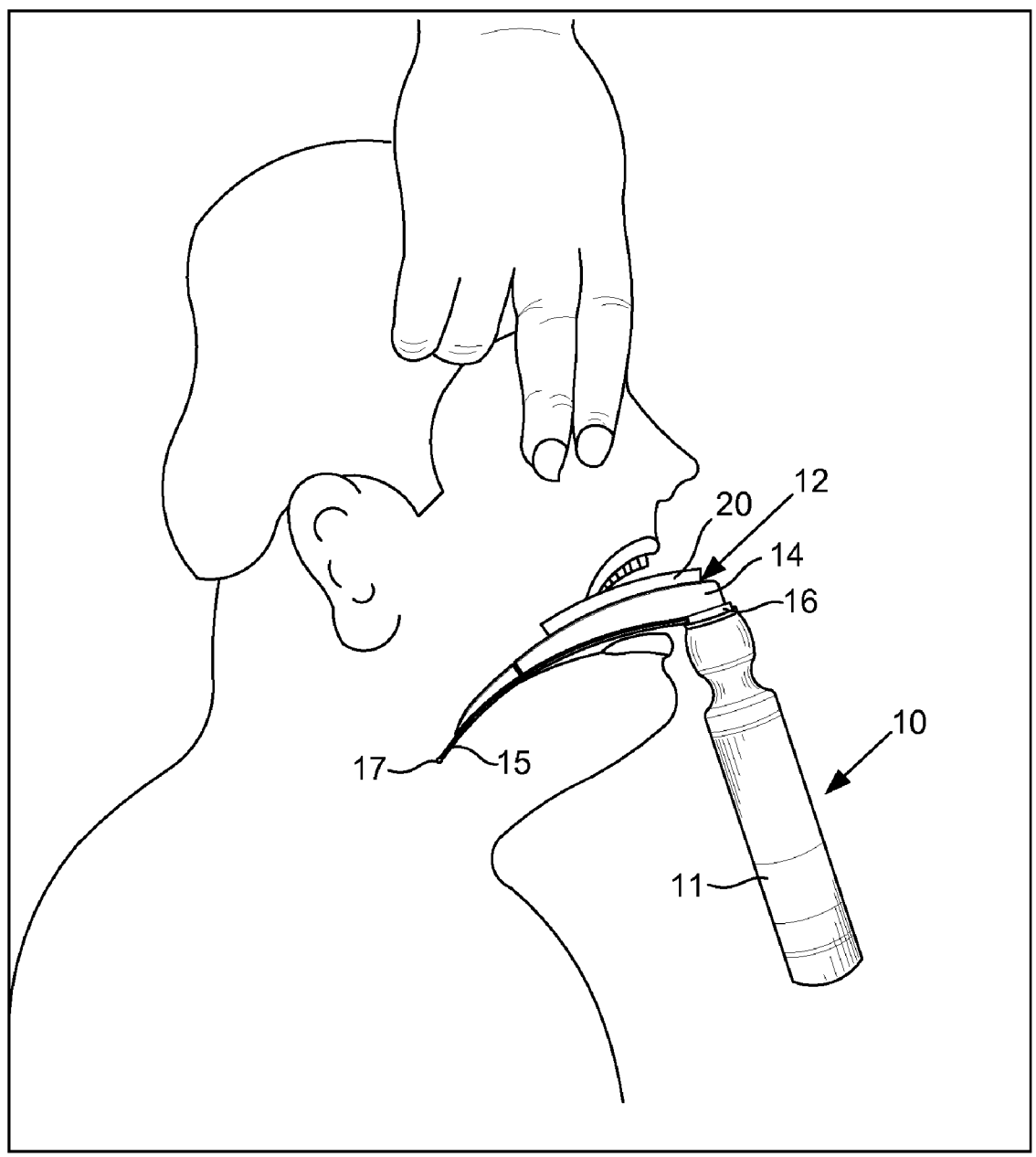
FIGS. 1 and 2 illustrate endotracheal intubation with a laryngoscope.
Figure 2:
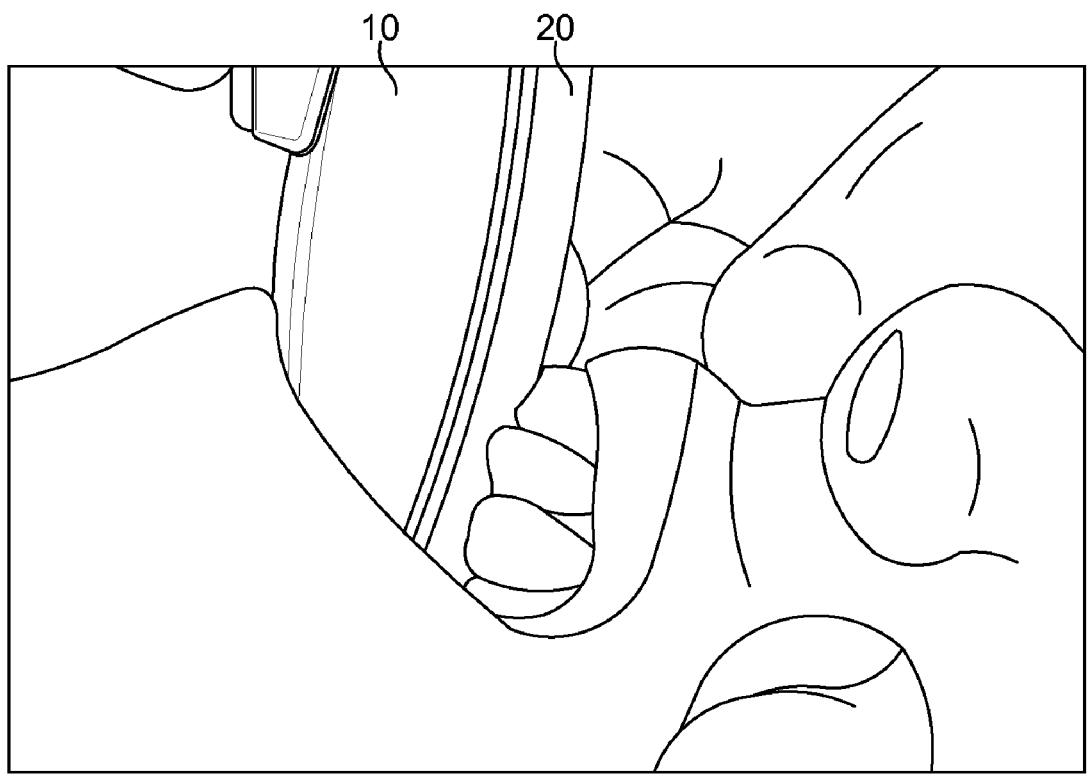

Referring to FIGS. 1 and 2, a physician uses a laryngoscope 10, which includes a handle 11 and a blade 12, to perform endotracheal intubation. The handle 11 contains a battery that is connected to a first electrical contact on the upper surface of the handle 11. The base 16 of the blade portion 15 is hinged to the top of the handle 11. The blade 12 carries an electric lamp 18 that is connected to a second electrical contact in the base 16 of the blade portion 15. When the blade 12 is swung upwards into its operating position, the first and second electrical contacts engage to illuminate the interior of the mouth with the electric lamp 18.

The blade 12 includes a lateral shelf 13, an upright wall 14 and a blade portion 15 which extends in the opposite direction of the shelf 13. The blade portion 15 is curved from its base 16 to its tip 17, the latter being in the form of a rounded transverse bar of the same width as the blade portion 15. The curvature of the blade portion 15 facilitates passage over the tongue and avoids depression of the tongue which otherwise might result in a restriction of the visible aperture of the larynx. The tongue is pushed to one side of the wall 14 and restrained in its movement by the shelf 13.

Figure 3:
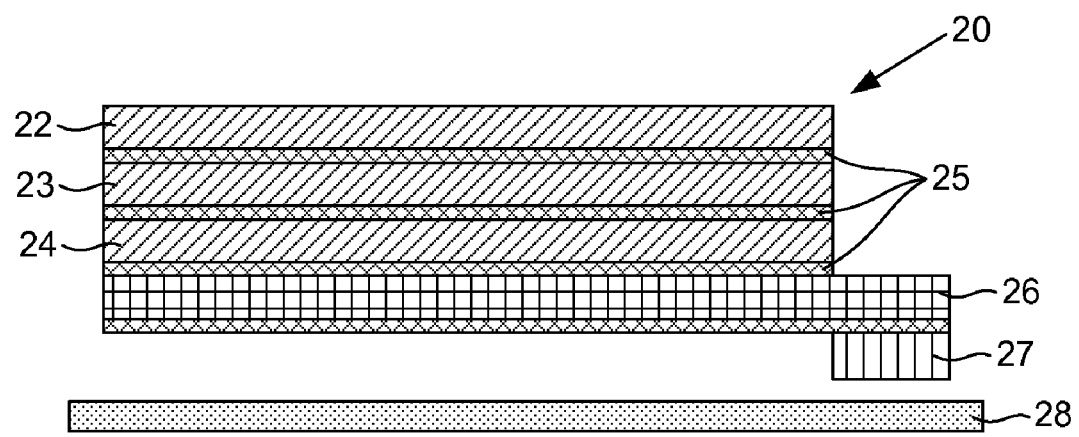
FIGS. 3 and 4 illustrate side and top views of a dental protection device.
Figure 4:
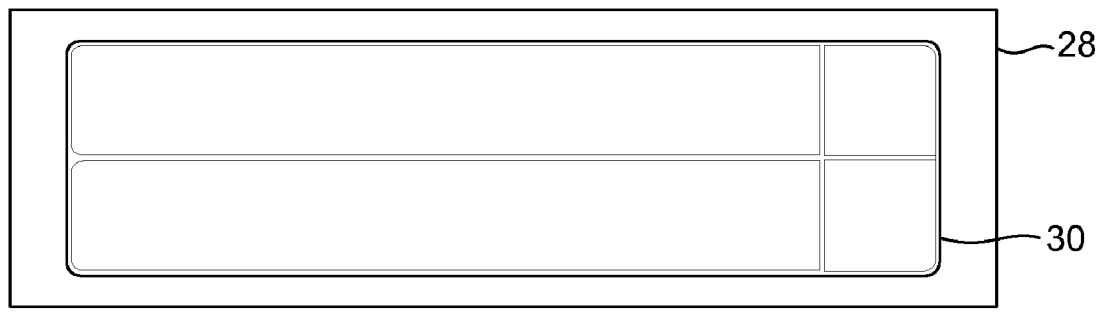

A dental protection device 20 is attached to the laryngoscope to protect the patient's teeth during the procedure. Referring to FIGS. 3 and 4, the dental protection device 20 is an elongated pad with a top surface and a bottom surface. In the embodiment shown in FIG. 3, the device 20 has three foam layers 22, 23, 24 that are bonded together to provide sufficient cushioning properties. The foam layers may have different density and/or compression characteristics. In still another embodiment, a single foam layer is used. An adhesive 26 is applied to the bottom surface and a pull-tab 27 is also attached to the bottom surface.

In the embodiment shown in FIG. 4, a pair of dental protection devices 30 is secured to a non-stick panel 28. The devices are split lengthwise so that the physician can use one or both devices 30. A cellophane wrapper (not shown) is positioned over the pair 30 and adhered to the non-stick panel 28.

The protection device 30 can be made of a foam material that is hypoallergenic and latex free. The pad or foam layers 23, 23, 24 are made of microfoam tape material with dimensions that can vary, such as, for example, 5.7 cm length×0.5 cm thickness×1.0 cm width. The tab 27 attached to the bottom surface is made of soft plastic.

The adhesive layer 26 has properties that make it easily peel away from the non-stick panel 28 but provide a secure bond when the device is adhered to a surgical instrument made of plastic or metal. However, after the surgical procedure is completed the device can be removed from the medical instrument without leaving behind a residue.

Figure 5:
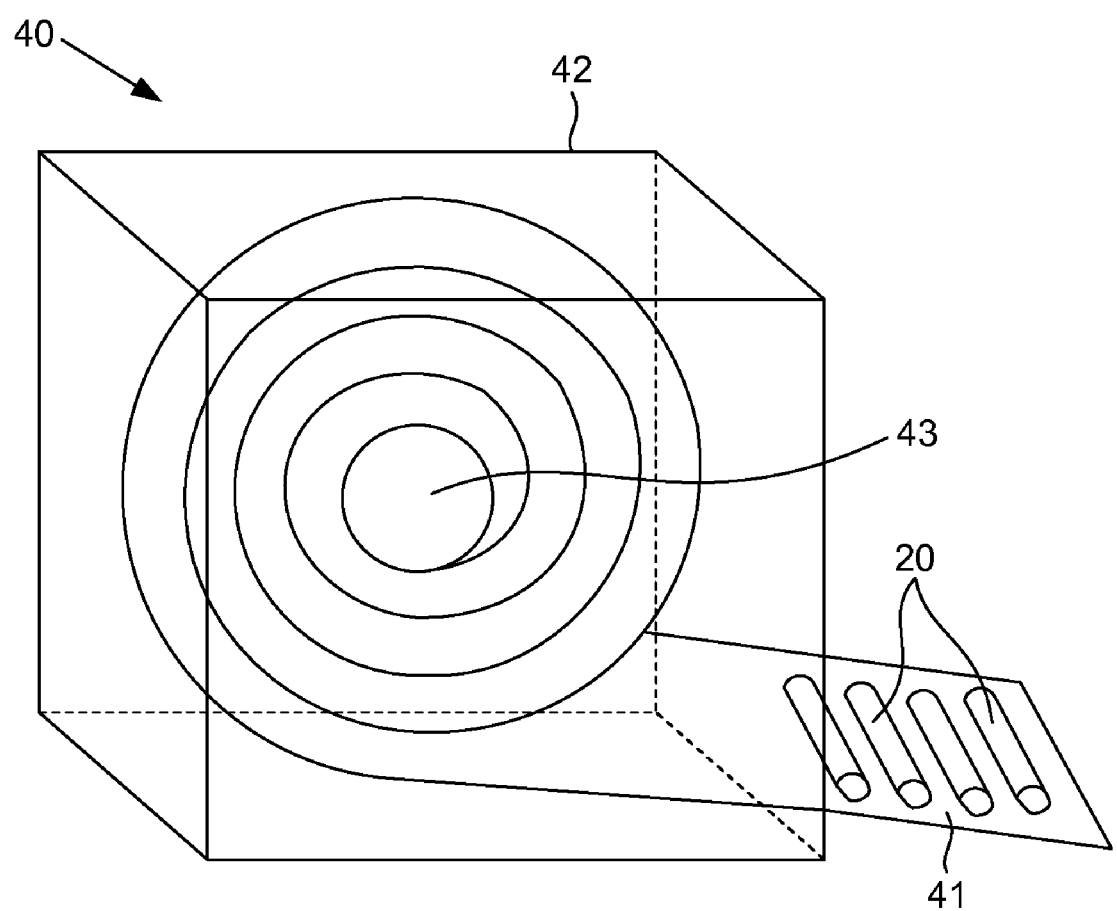
FIG. 5 illustrates a dental protection system in an enclosed box.

FIG. 5 shows an alternative dental protection system 40 with a series of the protection devices 20 in an enclosed box 42. The protection devices 20 are adhered to a long rectangular strip 41 with a non-stick surface, with the length of each device positioned perpendicular to the length of the strip 41.

The rectangular strip 41 has one end fastened to a dowel 43 and it is repeatedly wrapped around the dowel 43. The dowel 43 is attached to the inside surfaces of the box 42 near its center. The dowel rotates so that the protection devices 20 can be dispensed though an opening or slit anywhere on the box 42.

The system 40 has the advantage of allowing the anesthesiologist to quickly access one or more protection devices 20. It is designed so that the physician can grasp the pull-tab with one hand to remove the protection device from the strip while holding a laryngoscope in the other hand. This makes the system 40 easy and fast to use during an emergency.

Figure 6:
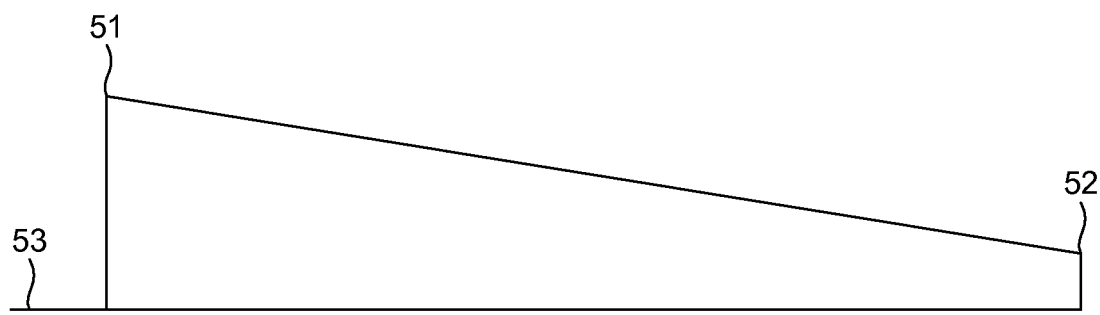
FIGS. 6 and 7 are side and perspective view of a tapered dental protection device.
Figure 7:
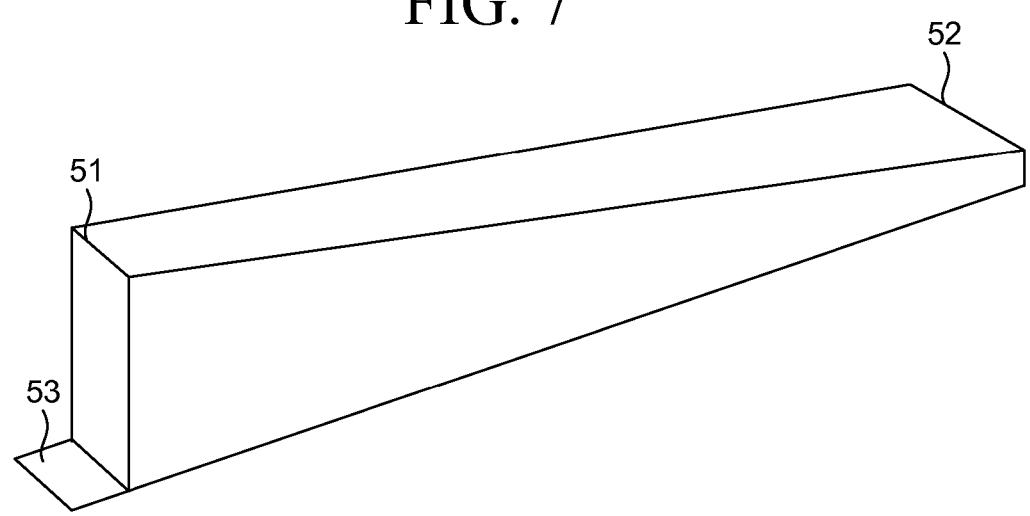

FIGS. 6 and 7 show another embodiment of the dental protection device 50. The end 51 of the pad at the tab 53 is very thick to provide maximum cushioning. The pad is tapered such that the opposing end 52 has minimal thickness.

The tapered end 52 is positioned near the tip 17 of the laryngoscope blade 15. Since the tapered end 52 has a low profile that becomes one with the flange, it does not impede the view, minimize the oral space or distract from the procedure. In addition, it cannot easily get caught on the patient's teeth and be dislodged when the tip 17 is advanced through the patient's mouth.

The description provided above explains how a dental protection device that is adhered to a laryngoscope helps to protect a patient's teeth from damage during an endotracheal intubation procedure. The embodiments that are described and illustrated above illustrate the principles of the present invention, however, other embodiments fall within the scope of the following claims.

We claim:

1. A dental protection system comprising:
    a laryngoscope including a blade and a handle extending from the blade;
    an elongated pad with a top surface and a bottom surface, the pad having a first foam layer, a second foam layer and a third foam layer, wherein the first foam layer is bonded to the second foam layer and the second foam layer is bonded to the third foam layer;
    an adhesive applied to at least a portion of the bottom surface; and
    a pull-tab attached to the pad to remove the elongated pad from a panel;
    wherein the elongated pad is adhered to the blade of the laryngoscope to prevent excessive pressure between the blade and a patient's teeth during an intubation procedure of a patient.

2. The system of claim 1, wherein the pad comprises a rectangular foam pad.

3. The system of claim 1, wherein the pad comprises a closed-cell foam pad.

4. The system of claim 1, wherein:
    the pad comprises a first end and a second end; and
    the tab is attached to the first end.

5. The system of claim 4, wherein the first end has a height greater than a height of the second end.

6. The system of claim 5, wherein the pad is tapered from the first end to the second end.

7. A dental protection system for endotracheal intubation during an anesthesia procedure, the system comprising:
- a dental protection device including an elongated pad with a top surface and a bottom surface, an adhesive applied to at least a portion of the bottom surface, and a tab attached to the elongated pad, wherein the elongated pad comprises a first foam layer bonded to a second foam layer and the second foam layer bonded to a third foam layer; and
- a laryngoscope with a blade and a handle extending from the blade;
- wherein the dental protection device is adhered to the blade to prevent excessive pressure between the blade and a patient's teeth during an intubation procedure of a patient;
- a rectangular strip with a non-stick surface;
- wherein more than one dental protection device is positioned on the non-stick surface.

8. A method of using a dental protection device for endotracheal intubation during an anesthesia procedure wherein the dental protection device includes an elongated pad having first, second and third foam layers bonded to each other, an adhesive backing and a pull-tab, the method comprising:
- providing the dental protection device with the elongated pad having first, second and third foam layers bonded to each other, the adhesive backing and the pull-tab;
- grasping the pull-tab;
- pulling the pull-tab to remove the dental protection device from a panel;
- adhering the dental protection device to a laryngoscope having a blade and a handle extending from the blade with the adhesive backing in contact with the blade of the laryngoscope; and
- inserting the blade of the laryngoscope in a patient's mouth wherein the dental protection device prevents excessive pressure on the patient's teeth when contact occurs between the patient's teeth and the laryngoscope blade.

9. The method of claim 8, further comprising:
- applying a second dental protection device to the opposing side of the blade.

* * * * *